an image (12) United States Patent
Goodwin (10) Patent No.: US 8,740,930 B2
(45) Date of Patent: Jun. 3, 2014

(54) EMBOLIC FILTER DEVICE INDEPENDENT OF TREATMENT DEVICE

(75) Inventor: Jonathan L. Goodwin, Nashua, NH (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 1437 days.

(21) Appl. No.: 12/392,141

(22) Filed: Feb. 25, 2009

(65) Prior Publication Data

US 2010/0217303 A1    Aug. 26, 2010

(51) Int. Cl.
*A61M 29/00*    (2006.01)

(52) U.S. Cl.
USPC .............................. 606/200; 606/127; 606/128

(58) Field of Classification Search
USPC .......... 606/200, 159, 127, 128; 604/104–107; 623/2.11
See application file for complete search history.

(56) References Cited

U.S. PATENT DOCUMENTS

| | | | |
|---|---|---|---|
| 5,814,064 A | | 9/1998 | Daniel et al. |
| 6,059,825 A | * | 5/2000 | Hobbs et al. .................. 623/1.18 |
| 6,824,545 B2 | * | 11/2004 | Sepetka et al. ................ 606/113 |
| 6,932,830 B2 | | 8/2005 | Ungs |
| 7,264,632 B2 | | 9/2007 | Wright et al. |
| 2005/0004598 A1 | * | 1/2005 | White et al. ................... 606/200 |
| 2005/0038468 A1 | | 2/2005 | Panetta et al. |
| 2007/0167665 A1 | * | 7/2007 | Hermann et al. .................. 600/3 |

* cited by examiner

*Primary Examiner* — Victor Nguyen
*Assistant Examiner* — Kevin Everage (57) ABSTRACT

A self-expanding filter for collecting emboli or thrombi in a vessel of a patient is disclosed. The filter has a tubular filter body that coils or spirals around an outer surface of an adjacently located, independent treatment device in a corkscrew fashion when deployed from a sheath delivery catheter. When fully deployed, an outer surface of the coiled tubular body conforms to the inner wall of the vessel and an inner surface of the coiled tubular body conforms to an outer surface of the treatment device. The treatment device is disposed within a longitudinal opening extending through the expanded, coiled tubular body of the filter during an interventional procedure.

18 Claims, 7 Drawing Sheets

EMBOLIC FILTER DEVICE INDEPENDENT OF TREATMENT DEVICE

FIELD OF THE INVENTION

The invention relates generally to intraluminal filtering devices for capturing particulate in the vessels of a patient. More particularly, the invention relates to a self-expanding filter for capturing emboli and/or thrombi in a blood vessel.

BACKGROUND OF THE INVENTION

Catheters have long been used for the treatment of diseases of the cardiovascular system, such as treatment or removal of stenosis. For example, in a percutaneous transluminal coronary angioplasty (PTCA) procedure, a catheter is used to transport a balloon into a patient's cardiovascular system, position the balloon at a desired treatment location, inflate the balloon, and remove the balloon from the patient. Another example of a common catheter-based treatment is the placement of an intravascular stent in the body on a permanent or semi-permanent basis to support weakened or diseased vascular walls, or to avoid closure, re-closure or rupture thereof.

These non-surgical interventional procedures often avoid the necessity of major surgical operations. However, one common problem associated with these procedures is the potential release of debris into the bloodstream that can occlude or embolize downstream vasculature and cause significant health problems to the patient. For example, during deployment of a stent, it is possible for the metal struts of the stent to cut into the stenosis and shear off pieces of atherosclerotic plaque which become embolic debris that can travel downstream from the interventional or surgical procedure and lodge somewhere in the patient's vascular system. Further, pieces of plaque or clot material can sometimes dislodge from the stenosis during a balloon angioplasty procedure and become entrained in the bloodstream.

Medical devices have been developed to attempt to deal with the problem created when debris or fragments are dislodged in the circulatory system during vessel treatment. One protection technique includes the temporary placement of an intravascular filter or trap downstream from the treatment site to capture debris before it can reach and embolize smaller blood vessels downstream. The placement of a filter in the patient's vasculature during treatment of a vascular lesion can collect embolic debris in the bloodstream. At the end of the vessel treatment, the filter can be removed along with the captured debris. Such filters typically comprise a filtration membrane, mesh or "basket" having a plurality of pores, each pore being sized to prevent passage of particulate larger than a certain size, e.g., 100-200 microns.

Conventionally, embolic filters are positioned downstream from the treatment device in a location that is distal to the treatment device with respect to the clinician. In such a distal location, the filter may be deployed in a location that does not interfere or interact with the proximally located treatment device. For example, it is known to attach an expandable filter to a distal end of a guidewire or guidewire-like member that allows the filtering device to be placed in the patient's vasculature. The guidewire allows the physician to steer the filter to a location downstream from the area of treatment. Once the guidewire is in proper position in the vasculature, the embolic filter can be deployed to capture embolic debris. Treatment devices then can be delivered to the area of treatment by tracking over the guidewire or guidewire-like member.

However, in some interventional procedures such as heart valve repair or replacement, it may be desirable to deploy an embolic filter in a location that is proximal to the treatment device with respect to the clinician. In such a proximal location, the treatment device may interfere with filter deployment. Thus, a need arises in the art for a filter system particularly suited for use in a valve repair or replacement procedure.

BRIEF SUMMARY OF THE INVENTION

Embodiments hereof are directed to a self-expanding filter for collecting embolic debris in a vessel of a patient. The filter has a tubular body, which may be formed from a plurality of woven filaments or of a tubular membrane with holes formed therein. When in a delivery configuration, the tubular body is substantially cylindrical. When in a deployed configuration, the tubular body coils into a series of one or more loops that define an outer surface of the coiled tubular body for conforming to an inner wall of the vessel and an inner surface of the coiled tubular body defining a longitudinal opening through the filter.

Embodiments hereof are also directed to a method for collecting embolic debris in a vessel of a patient during an interventional procedure. An independent treatment device is positioned at a target location in the vessel. A self-expanding filter having a tubular body in a delivery configuration is also positioned at the target location in the vessel. The filter is deployed to an expanded configuration in which the tubular body coils into a series of one or more loops that spiral around an outer surface of the independent treatment device in a corkscrew fashion such that an outer surface of the coiled tubular body conforms to a vessel wall defining the body lumen and an inner surface of the coiled tubular body conforms to the outer surface of the independent treatment device. The interventional procedure is performed with the treatment device, wherein embolic debris from the interventional procedure is collected within the deployed filter.

BRIEF DESCRIPTION OF DRAWINGS

The foregoing and other features and advantages of the invention will be apparent from the following description of embodiments of the invention as illustrated in the accompanying drawings. The accompanying drawings, which are incorporated herein and form a part or the specification, further serve to explain the principles of the invention and to enable a person skilled in the pertinent art to make and use the invention. The drawings are not to scale.

DETAILED DESCRIPTION OF THE INVENTION

Specific embodiments of the present invention are now described with reference to the figures, wherein like reference numbers indicate identical or functionally similar elements. When discussing features of the embolic filtering system described herein, the terms "distal" and "proximal" are used with respect to a position or direction relative to the treating clinician. More particularly, "distal" or "distally" are a position distant from or in a direction away from the clinician and "proximal" and "proximally" are a position near or in a direction toward the clinician. However, when discussing positions of tile embolic filtering system and/or the independent treatment devices within the aorta proximate the heart, the terms "distal" and "proximal" are used in the following description with respect to the heart. More particularly, "distal" or "distally" are a position away from the heart and "proximal" or "proximally" are a position near or closer to the heart.

The following detailed description is merely exemplary in nature and is not intended to limit the invention or the application and uses of the invention. Although the description of the invention is in the context of treatment of heart valves or blood vessels such as the aorta or the coronary, carotid and renal arteries, the invention may also be used in any other body passageways where it is deemed useful. Furthermore, there is no intention to be bound by any expressed or implied theory presented in the preceding technical field, background, brief summary or the following detailed description. The invention can be used with current or future heart valve repair or replacement devices, stent systems, balloon catheters, or any other treatment devices where it is deemed useful.

Figure 1:
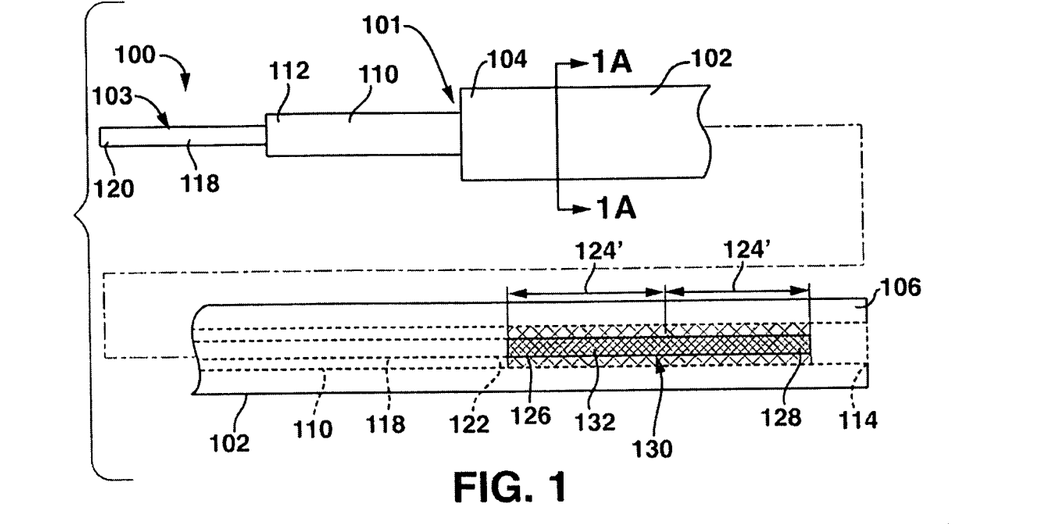
FIG. 1 is a schematic side view of an embodiment of an embolic filtering system having a filter at a distal portion thereof, wherein the filter is in a collapsed or delivery configuration.
Figure 1A:
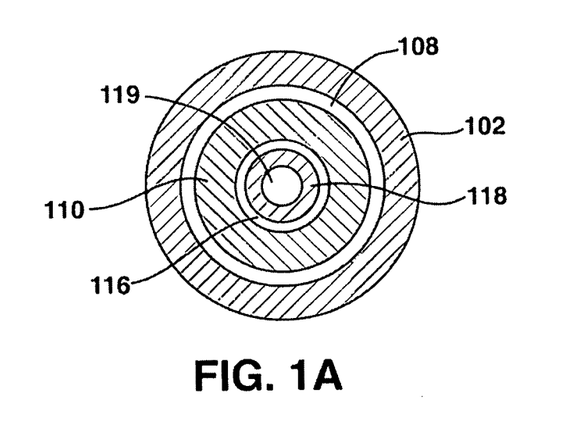
FIG. 1A is a cross-sectional view of the embolic filtering system taken along line A-A of FIG. 1.

FIG. 1 is a schematic side view of an embolic filtering system 100 for delivering a filter 130 in a collapsed or delivery configuration, while FIG. 1A is a cross-sectional view taken along line A-A of FIG. 1. Embolic filtering system 100 includes a delivery catheter 101 with a filtering component 103 slidably contained therein. Delivery catheter 101 includes an outer sheath 102 having a proximal end 104, a distal end 106, and a lumen 108 extending therethrough and an inner sheath 110 having a proximal end 112, a distal end 114, and a lumen 116 extending therethrough. Inner sheath 110 slidably extends through lumen 108 of outer sheath 102. Filtering component 103 slidably extends within lumen 116 of inner sheath 110 and includes an elongate shaft 118 with a lumen 119 extending therethrough and having filter 130 mounted thereon. The filter 130 is collapsed or compressed inside the inner sheath 110 and contacts the inner sheath 110. A proximal end 126 of filter 130 distally extends from a distal end 122 of elongate shaft 118, and an unattached or free distal end 128 of filter 130 forms the distal end of filtering component 103. Filter proximal end 126 is fixedly attached to elongate shaft 118 by spot welding, laser welding, suturing, using an adhesive or by any other suitable means known to one of skill in the art of catheter construction. Filter distal end 128 defines an open end of lumen 119. Filter shaft 118 may be a tubular component defining lumen 119 for receiving a guidewire (not shown) therethrough, or may alternatively be a solid rod to provide additional pushability to embolic filtering system 100. In the alternative embodiment wherein filter shaft 118 is a solid rod, filter distal end 128 may be closed (not shown), as by constricting or bundling and tying off or otherwise sealing the distal end of filter 130. Proximal ends 104, 112, 120 of outer sheath 102, inner sheath 110, and filter shaft 118, respectively, each extend proximally outside of the patient's body such that they may be manipulated by the physician and may include a handle or knob (not shown) in order to facilitate securing a longitudinal position or sliding movement thereof.

Filter 130 is a self-expanding component having a tubular body 131 that defines an interior volume 129 (best shown in FIG. 6A) and has a generally circular cross-section, wherein the tubular body 131 is formed from a plurality of filaments or wires 132 that are braided or woven together. When filter 130 is partially deployed or expanded within a vessel, tubular body 131 coils or winds to form a series of one or more loops 124 that spiral around an indwelling catheter or treatment device and then fully deploys or expands to span the annular space between the catheter or device and a wall of the vessel, as discussed in detail below. In another embodiment, filter 130 may be formed from a suitable mesh or porous material, such as filter 930 described in more detail below, having a laser drilled membrane with openings of between 40-500 microns. In still further embodiments, filter 130/930 may have openings of between 50-100 microns or 75-125 microns. When fully deployed or expanded, filter 130 collects embolic debris within interior volume 129 of at least one loop 124 of tubular body 131 and/or within spaces between braided filaments 132 while simultaneously permitting fluid to flow therethrough, such as an amount of blood flow sufficient for perfusion of body tissues.

Figure 2:
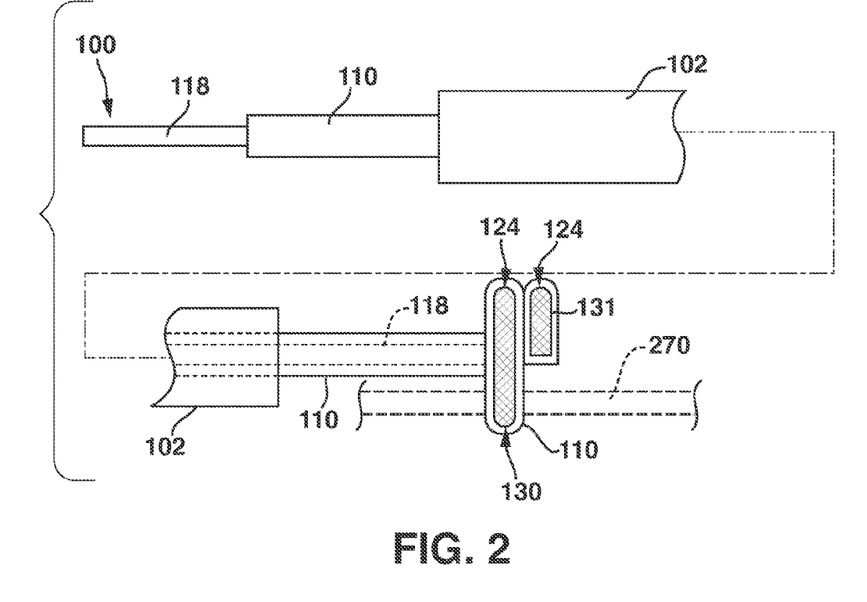
FIG. 2 is a schematic side view of the embolic filtering system of FIG. 1, wherein the filter is in a partially deployed or expanded configuration after an outer sheath of the embolic filter system is retracted.
Figure 3:
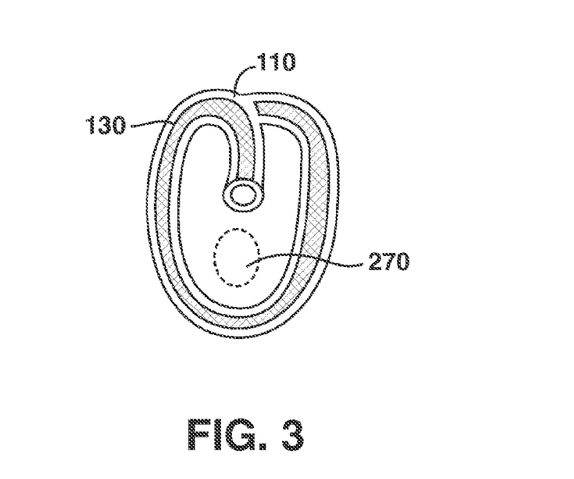
FIG. 3 is a schematic end view of FIG. 2.

Outer and inner sheaths 102, 110 are provided to constrain and support filter 130 in a collapsed, delivery configuration and a partially deployed configuration, respectfully. More particularly, outer sheath 102 longitudinally holds tubular body 131 of filter 130 and inner sheath 110 in a relatively straight, cylindrical profile during delivery to ease advancement of embolic filtering system 100 through the vasculature to the treatment site within a body vessel, as shown in the delivery configuration in FIG. 1. While inner sheath 110 also concentrically holds tubular body 131 of filter 130 in a reduced profile, the main purpose for doing so is to provide sufficient columnar stiffness in filter tubular body 131 to give the component adequate rigidity to spiral and form one or more loops around an adjacently located, independent treatment device when outer sheath 102 is retracted, as shown in the partially deployed configuration in FIGS. 2 and 3. More particularly, inner sheath 110 provides radial constraint of filter 130 while being longitudinally flexible enough to be deformed or guided into the looped shape by filter 130 there within, filter 130 having been preformed to assume a predetermined or heat-set shape.

In an alternate embodiment of filtering system 100, the inner sheath 110 is preformed to assume a predetermined or heat-set shape when the outer sheath 102 is retracted. In this embodiment, the filter 130 may or may not have a predetermined or heat-set shape. Thus, filter 130 is deployable in a series of loops wherein either filter 130, inner sheath 110 or both components are preformed.

In order to radially constrain tubular body 131 of filter 130 while allowing the tubular body to assume its partially expanded coiled shape, inner sheath 110 may be formed from a flexible polymeric tubing such as tubing of polyethylene terephthalate (PET), polypropylene, nylon, polyethylene, polyether block amide (PEBA), fluoropolymers such as polytetrafluoroethylene (PTFE) or fluorinated ethylene propylene (FEP), or combinations thereof. Outer sheath 102 may also be formed from a flexible polymeric tubing such as tubing of PET, polypropylene, nylon, polyethylene, PEBA, PTFE, FEP or combinations thereof.

Accordingly, the deployment of filter 130 occurs in a multi-step process in which outer sheath 102 is initially retracted from around tubular body 131 for partial deployment/expansion of filter 130, and inner sheath 110 is subsequently retracted from around tubular body 131 for full deployment/expansion of filter 130. With only outer sheath 102 retracted, an outer diameter of tubular body 131 of filter 130 is still radially compressed or reduced by inner sheath 110. Inner sheath 110 having filter 130 therein assumes a predetermined or heat-set shape of filter 130 in which tubular body 131 winds in a series of one or more loops 124 around an outer surface of an independent treatment device 270 (shown in phantom in FIGS. 2 and 3) in a helical or corkscrew fashion. In this manner, filter 130 is deployed around and encircles independent treatment device 270. "Independent treatment device" as used herein refers to a device that is not attached or connected to embolic filter system 100 and is delivered to the target site separately from the embolic filter system. Independent treatment device 270 may be, for example, a heart valve repair or replacement device, a stent delivery catheter, a balloon catheter or a guide wire.

Figure 5:
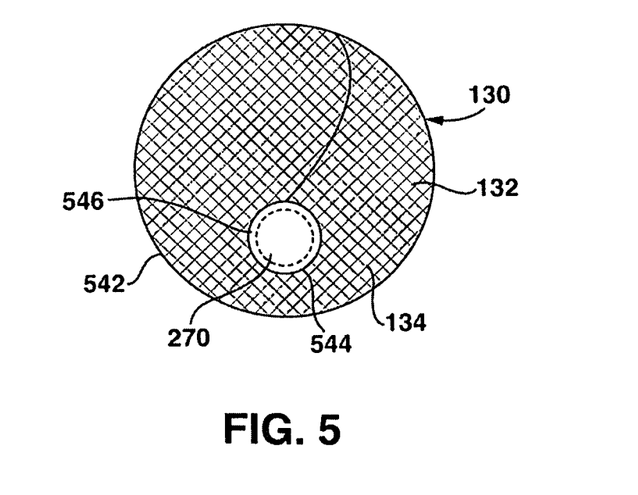
FIG. 5 is a schematic end view of FIG. 4.
Figure 6A:
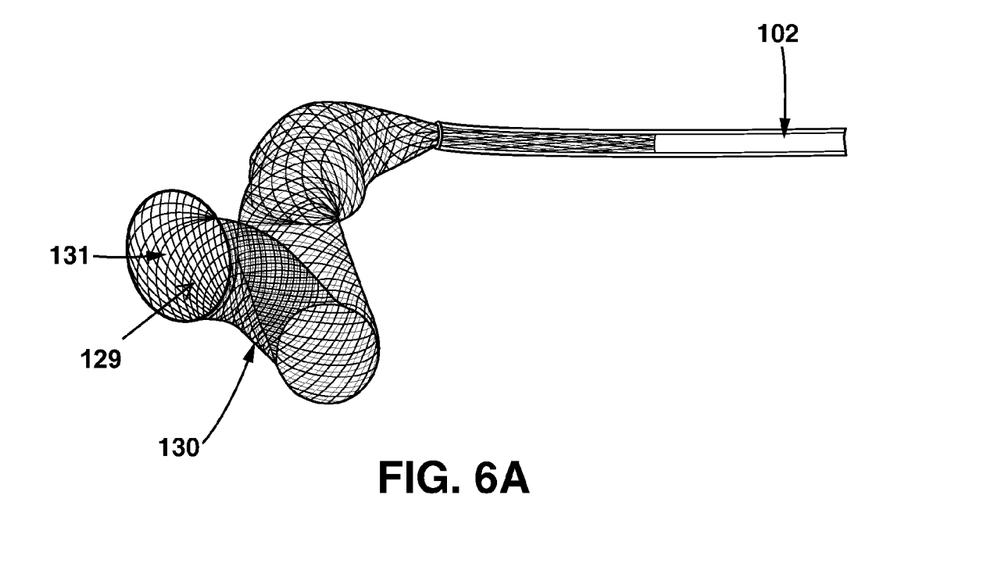
FIGS. 6A and 6B are photographs of a braided filter precursor, which is an unfinished filter, being deployed according to one embodiment hereof.
Figure 6B:
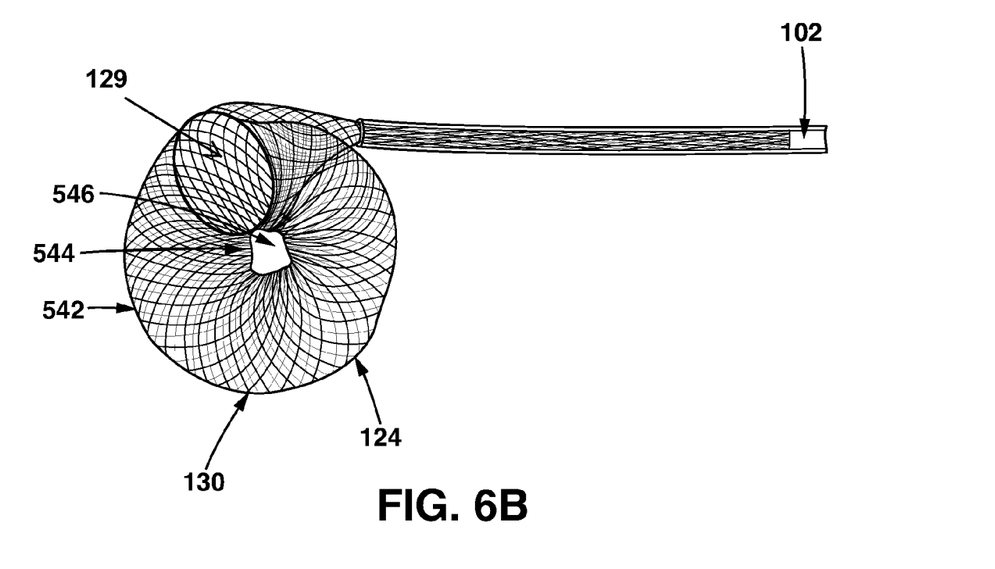

With inner sheath 110 proximally retracted to expose tubular body 131, the outer diameter of tubular body 131 of filter 130 self-expands into the fully expanded/deployed configuration such that an outermost surface 542 of at least one loop 124 will conform to the vessel wall and an innermost surface 544 of at least one loop 124 will conform to an outer surface of independent treatment device 270 (shown in phantom in FIGS. 4 and 5) located within a longitudinal opening 546 that extends through the expanded, coiled tubular body 131 (best shown in FIG. 6B). A single winding or loop 124 of the deployed form of tubular filter 130 may also be described mathematically as a helical torus wherein the generally toroidal or "doughnut" shape is formed out of plane by one turn of a helix. A precursor of filter 130 is depicted in the photographs of FIGS. 6A and 6B, wherein filter precursor 130' is shown with outer sheath 102 partially retracted and without inner sheath 110 for sake of clarity. It should be noted that filter precursor 130' has an unfinished distal end and has not yet been modified to have enlarged pores in an upstream surface. Consecutive or adjacent loops 124 of coiled tubular body 131 each have the same expanded outer diameter such that the fully deployed filter 130 forms a longitudinally-extending cylindrical profile that spans the annular space between device 270 and the vessel wall. In addition, the spacing between adjacent loops 124 is zero or sufficiently small to prevent embolic debris from escaping therebetween. Thus, in the fully deployed configuration, expanded filter 130 operates to collect embolic debris that may come loose and flow downstream during operation of independent treatment device 270.

Figure 4:
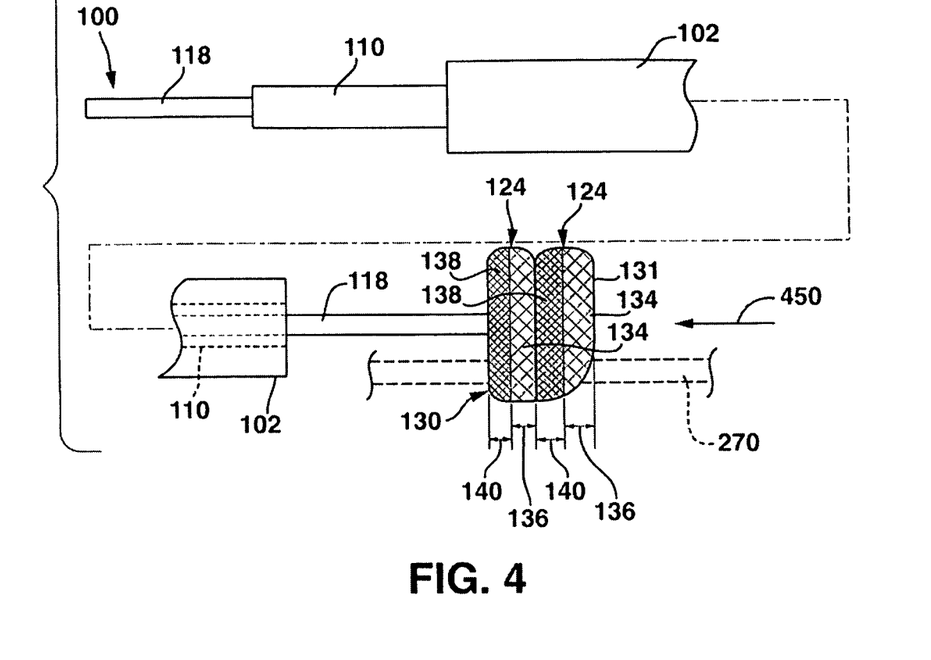
FIG. 4 is a schematic side view of the embolic filtering system of FIG. 1, wherein the filter is in a fully deployed or expanded configuration after both an outer sheath and an inner sheath of the embolic filter system are retracted.

As best shown in FIG. 4, to provide the filtration function when filter 130 is fully deployed, first openings 134 of upstream-facing sections 136 of loops 124 of tubular body 131 are sized to allow passage of particulate dislodged from the treatment site into interior volume 129 of the loops 124. To retain or capture the plaque particulate within interior volume 129 of loops 124, second openings 138 of downstream-facing sections 140 of loops 124 of tubular body 131 are sized to prevent the captured particulate from exiting the loop downstream thereby providing embolic protection during the interventional procedure. Thus, second openings 138 in downstream-facing sections 140 of loops 124 are of a smaller dimension than first openings 134 in upstream-facing sections 136 of loops 124.

In the embodiment depicted in FIG. 4, filter 130 has two loops 124 but it should be understood that the filter 130 may include one, two, or more than two loops 124. In addition, upstream-facing sections 136 with first openings 134 and downstream-facing sections 140 with second openings 138 are each shown being approximately half of the torus that essentially defines each loop 124, i.e., half of the surface area of each generally toroidal or "doughnut" shaped loop 124. In another embodiment, upstream-facing section(s) 136 with first openings 134 may comprise more or less than half the surface of torus-defining loop(s) 124, as long as there are sufficient first openings 134 to allow capture of the particles and sufficient second openings 138 in downstream-facing section(s) 140 to retain the particles inside loop(s) 124. Additionally, downstream-facing section(s) 140 with second openings 138 may comprise more or less than half the surface of torus-defining loop(s) 124 as long as the particles are contained in the loop(s) 124. There also may be third openings (not shown) disposed in a transition region with openings of a size between first and second openings 134, 138.

In addition, loops 124 are shown in FIG. 4 as each being approximately half of an axial length of coiled filter 130. The axial length of a loop or coil 124 is a function of its arc length 124', which is illustrated in the straightened-out configuration of filter 130 shown in FIG. 1. In another embodiment, loops 124 may be of unequal lengths.

In FIG. 4 vessel walls have been omitted for clarity, but blood flow direction is indicated by arrow 450, herein referred to as a retrograde application as may be used in the aorta during a heart valve replacement procedure such as that described with reference to FIGS. 7 and 8. In the embodiment of FIGS. 1-5 (best shown in FIG. 4), upstream-facing segments 136 are located on a distal portion of each loop 124 of filter 130 and downstream-facing segments 140 are located on a proximal portion of each loop 124 of filter 130 such that, as blood flows through expanded filter 430 in the direction indicated by arrow 450, embolic debris may pass through first opening(s) 134 of upstream-facing segments 136 into the interior of coiled tubular body 131 of filter 130 to be trapped therein by second, smaller sized openings 138 of downstream-facing segments 140. In another embodiment where an embolic filtering system in accordance herewith is to be used in an antegrade application, i.e., within a body vessel where blood flows in a direction opposite from that shown in FIG. 4, the coil shape of filter 130 may alternatively be constructed to have a distal portion of each loop with smaller dimensioned openings for retaining embolic debris and a proximal portion of each loop having one or more openings sized to allow the entry of embolic debris into coiled tubular body 131 of filter 130.

Figure 10:
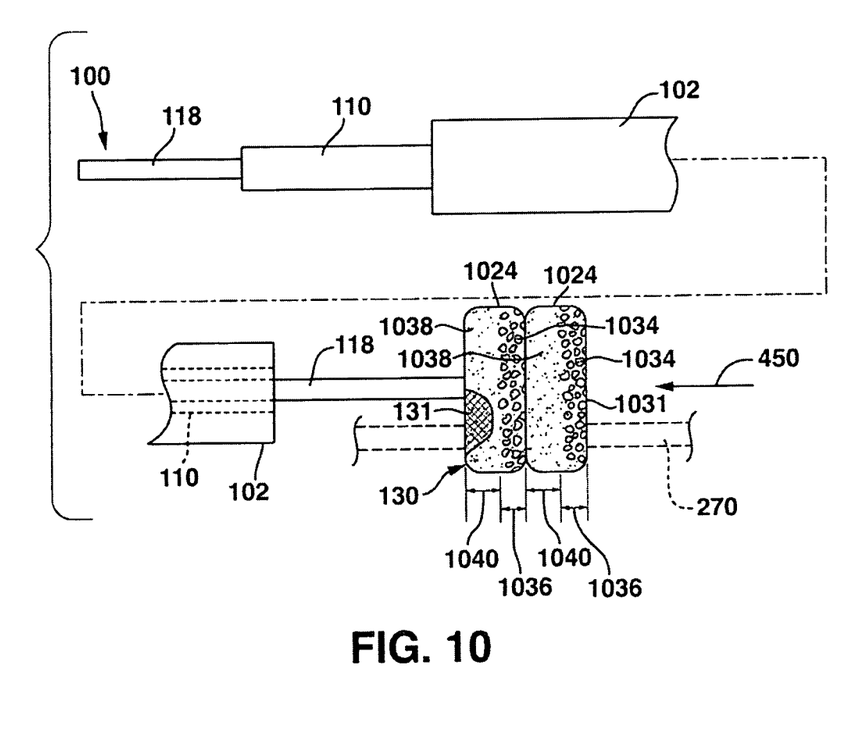
FIG. 10 is a schematic side view of an embolic filtering system according to another embodiment hereof, wherein the filter is in a fully deployed or expanded configuration after both an outer sheath and an inner sheath of the embolic filter system are retracted.

FIG. 10 depicts an alternate embodiment of embolic filtering system 100 with a self-expanding filter element 1030, where reference numbers for features previously described with reference to the embodiment of FIGS. 1-5 remain the same. Filter 1030 is formed from a tubular, porous, elastic membrane 1031 that covers braided tubular body 131, which is preformed to expand into loops 1024 upon deployment. In FIG. 10, a portion of membrane 1031 is removed for purposes of illustration to reveal underlying braided tubular body 131. Biocompatible elastic materials that are suitable for forming tubular membrane 1031 are silicone monomers, silicone polymers, silicone-urethane copolymers or other polymers which may include, but are not limited to, viscous forms of natural and synthetic rubbers such as polybutylene, polyisobutylene, polybutadiene, polyethylene-containing compounds, styrene-butadiene-styrene, styrenebutadiene copolymers, polyisoprene, polyurethane, ethylene/propylene copolymers, polyalkylacrylate polymers, copolyesters, ethylene/acrylic copolymers, and butadiene/acrylonitrile copolymers and other polymers such as ethylene vinylacetate (EVA) polymers.

Tubular membrane 1031 has first holes or openings 1034 in upstream-facing sections 1036 of loops 1024 that are sized to allow passage of particulate dislodged from the treatment site into an interior volume of the loops 1024. Further to permit perfusion and to capture the plaque particulate within the interior volume of loops 1024, tubular membrane 1031 has second holes or openings 1038 in downstream-facing sections 1040 of loops 1024 that are sized to prevent the captured particulate from exiting the loop downstream, thereby providing embolic protection during the interventional procedure. Thus, second openings 1038 in downstream-facing sections 1040 of loops 1024 are of a smaller dimension than first openings 1034 in upstream-facing sections 1036 of loops 1024. Braided tubular body 131 supports membrane 1031, and the interstices formed by braided filaments 132 may be larger than first openings 1034 formed in membrane 1031 so that the filaments 132 are less likely to interfere with the ingress of particulates through the first openings 1034 or the egress of blood through the second openings 1038.

In the embodiment of FIG. 10, upstream-facing sections 1036 with first openings 1034 comprise less than half the torus defining each loop 1024, whereas downstream-facing sections 1040 with second openings 1.038 comprise slightly more than half the torus defining each loop 1024. In alternate embodiments, as mentioned above, the coverage of the upstream-facing and downstream-facing sections 1036, 1040 with their respective sized openings 1034, 1038 may be equal or otherwise varied with respect to each loop 1024 without departing from the scope of the present invention. In an embodiment, openings 1034, 1038 may be made in the film or membrane that forms tubular membrane 1031 by laser-drilling as would be understood by one of ordinary skill in the art of embolic filter design.

Self-expanding as used herein means that filter 130 has a mechanical memory to return to an expanded or deployed configuration. Mechanical memory may be imparted to the braided wire or tubular structure that forms filter 130/930 by thermal treatment to achieve a spring temper in stainless steel, for example, or to set a shape memory in a susceptible metal alloy, such as nitinol, or a polymer, such as any of the polymers disclosed in U.S. Pat. Appl. Pub. No. 2004/0111111 to Lin, which is incorporated by reference herein in its entirety. Thus, in embodiments hereof braiding wires 132 for producing filter 130 may be made from stainless steel, a pseudo-elastic metal such as nitinol, or a so-called super alloy, which may have a base metal of nickel, cobalt, chromium, or other metal. In an embodiment hereof, second openings 138 are the size of interstices of the braided filter body 131. First openings 134, which are larger than second openings 138, are sized by the insertion of pins into certain interstices of the braided filter body 131 during the heat-setting process to selectively enlarge those openings.

A method of utilizing embolic filtering system 100 according to an embodiment hereof is described with reference to FIGS. 7, 8 and 8A. The following method of delivering filter 130 is described in relation to a catheter-based heart valve procedure in the location of the aortic valve and aortic arch, in which it is desirable to deploy an embolic filter in a location downstream and distal to a valve repair treatment device with respect to the heart yet proximal to the clinician relative to the valve treatment device. According to embodiments hereof, the filter is deployed around the valve treatment device such that the treatment device is positioned through the expanded filter during the interventional procedure. However, it will be understood that the method may be utilized for delivering a filter within other vasculature areas. The deployment dimensions of the expanded filter may vary according to clinical application.

Figure 7:
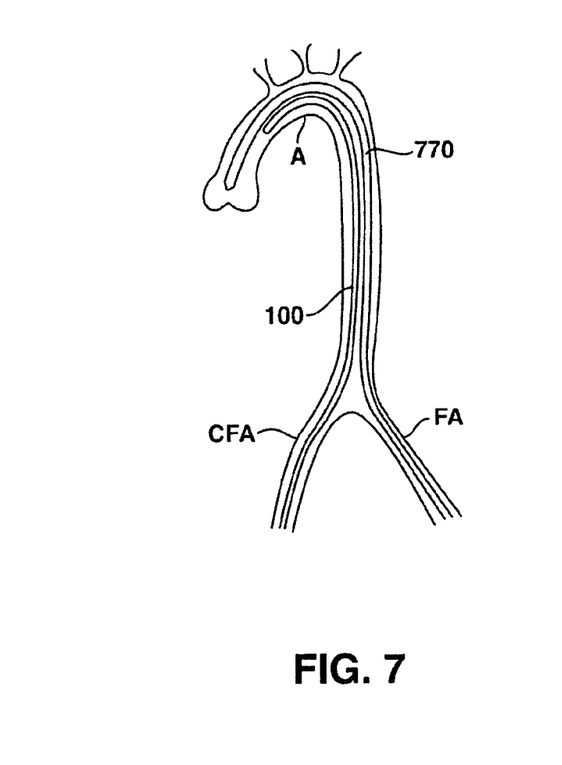
FIGS. 7-8 illustrate a method of utilizing the embolic filtering system of FIG. 1 in situ according to an embodiment hereof.
Figure 8:
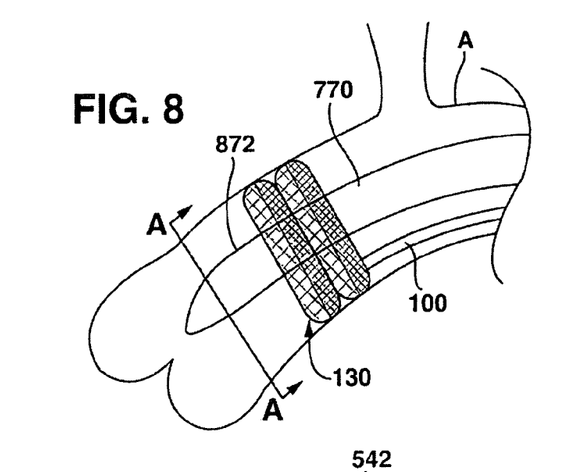
Figure 8A:
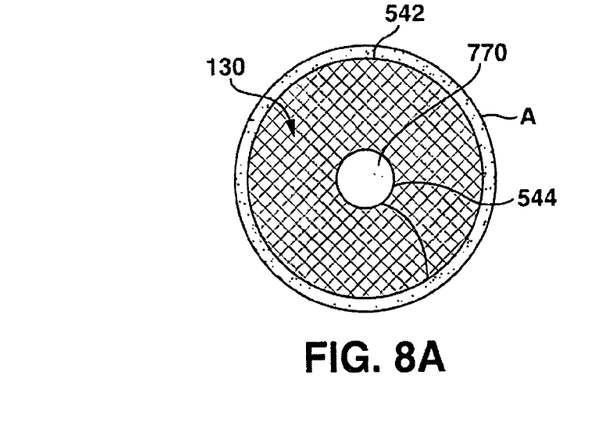
FIG. 8A is a cross-sectional view taken along line A-A of FIG. 8.

FIGS. 7 and 8 illustrate a treatment catheter 770 for use in a heart valve replacement procedure and an embolic filtering system 100 having filter 130 contained therein, which have been separately delivered within the aorta A distal of the aortic valve where filter 130 will be deployed to collect embolic debris that may come loose and flow downstream during the valve replacement procedure. An exemplary suitable treatment catheter 770 for delivering a replacement valve is described in U.S. Pat. No. 7,264,632 to Wright et al., which is hereby incorporated by reference in its entirety. Treatment catheter 770 and embolic filtering system 100 are introduced into the vasculature at separate sites, either via a percutaneous puncture, a.k.a the Seldinger technique, or via a surgical cut-down. More particularly, treatment catheter 770 is positioned at the aortic treatment site via a retrograde approach through a branch of the femoral artery FA, and embolic filtering system 100 is positioned at the aortic treatment site via a retrograde approach through a branch of the contralateral femoral artery CFA. Alternatively, treatment catheter 770 or embolic filtering system 100 may achieve access to the vasculature through a carotid artery, a subclavian artery, or a brachial artery. Methods and apparatus for accessing the arterial system with catheters and navigating such catheters to the level of the aortic arch are generally known in the art.

Once both treatment catheter 770 and embolic filtering system 100 are positioned as desired, outer sheath 102 of embolic filtering system 100 is first retracted to release filter 130 from a straightened, delivery configuration. With outer sheath 102 removed therefrom, filter 130 partially deploys to a predetermined shape in which the tubular body 131 of filter 130 coils into a series of one or more loops. Inner sheath 110 having filter 130 radially compressed therein permits the coiled shape of partially deployed filter 130 to be assumed by maintaining adequate stiffness in the partially expanded tubular body 131 such that one or more loops of the coiled tubular body may spiral around an outer surface 872 of treatment catheter 770. Alternatively, inner sheath 110 can have a preset coiled shape, by heat setting for example, so that when outer sheath 102 is removed, the inner sheath 110 and filter 130 assume the preformed, coiled shape of the inner sheath. Inner sheath 110 of embolic filtering system 100 is then retracted such that filter 130 self-expands to its fully deployed/expanded configuration, illustrated in FIGS. 8 and 8A. In its fully deployed configuration, outermost surface 542 of the coiled tubular body 131 conforms and seals to the aortic vessel inner wall and innermost surface 544 of the coiled tubular body 131 conforms and seals to outer surface 872 of treatment catheter 770 such that filter 130 encircles and extends around the entire circumference of treatment catheter 770 to span the annular space between treatment catheter 770 and the aortic vessel inner wall.

Once filter 130 is fully deployed, treatment catheter 770 is utilized for valve replacement according to its operation.

During the valve procedure, filter 130 operates to collect embolic debris within the interior volume of at least one winding or loop 124 of coiled filter body 131. When the valve procedure is complete, treatment device 770 is at least partially withdrawn or retracted to a point proximal of expanded filter 130. In one embodiment, treatment catheter 770 may be completely removed from the body before collapsing and removing filter 130. Filter 130, which may now contain embolic debris within coiled tubular body 131, is then collapsed by advancing outer sheath 102 over filter 130. Alternatively, a separate sheathing device (not shown), different from sheath 102, may be advanced thereover to collapse filter 130. The sheathing step not only captures and compresses filter 130 such that it may be removed from the body, but also captures the particles of embolic debris that may be contained within filter 130. Lumen 108 of sheath 102 is larger than lumen 116 of inner sheath 110 through which filter 130 was delivered. Therefore, collapsing filter 130 within lumen 108 of sheath 102 for withdrawal is not expected to squeeze debris out of open filter distal end 128. The alternative embodiment wherein filter distal end 128 is closed is expected to be further capable of preventing loss of debris upon collapsing filter 130. Embolic filtering system 100, including collapsed filter 130, is then retracted from the patient's vasculature.

The above-described method includes positioning both embolic filtering system 100 and valve repair treatment catheter 770 within the vasculature, and subsequently deploying filter 130 such that its tubular body 131 coils around the outer surface of the valve repair treatment catheter 770. Alternatively, embolic filtering system 100 may be positioned and deployed at the target site before introduction of the valve repair treatment catheter 770. In such an embodiment, self-expanding filter 130 would be formed to coil within the vasculature leaving a longitudinal opening therethrough such that once filter 130 is deployed, treatment device 770 may be threaded through the longitudinal opening of deployed filter 130 and utilized for valve replacement according to its operation.

Figure 9:
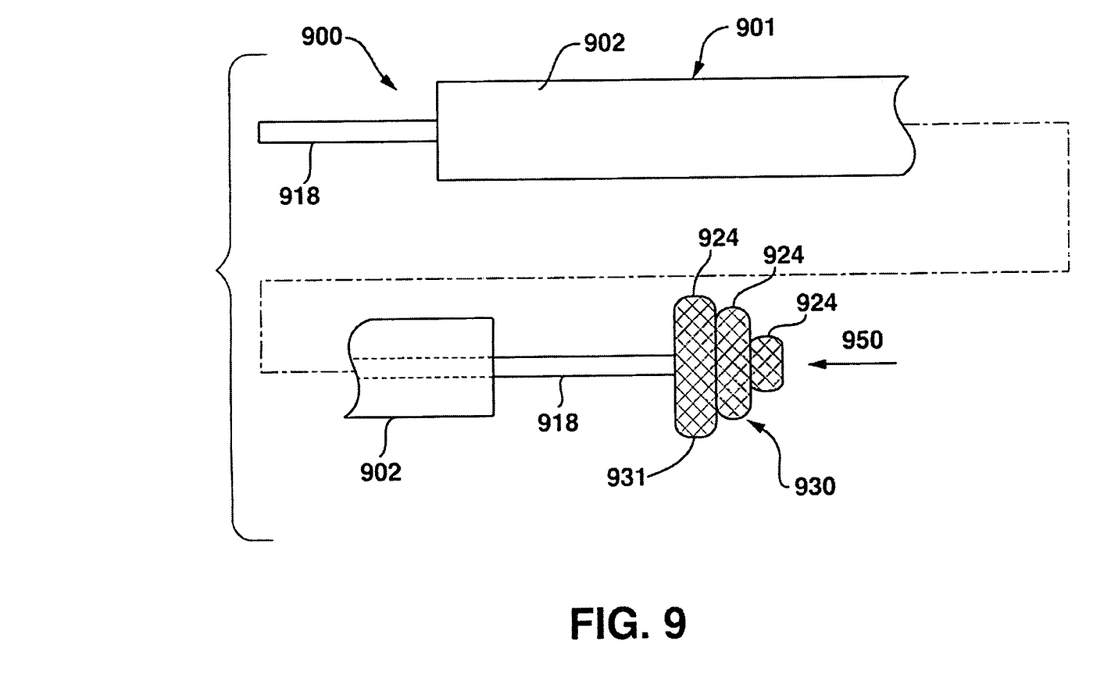
FIG. 9 is a schematic side view of an embodiment of an embolic filtering system having a filter at a distal portion thereof according to another embodiment hereof.

FIG. 9 is a schematic side view of an embodiment of an embolic filtering system having a filter 930 at a distal portion thereof according to another embodiment of the invention. In the embodiment of FIG. 9, the inner sheath component described above with respect to FIGS. 1-5 is omitted and tubular body 931 of filter 930 is formed from a sufficiently stiff material that the tubular body will coil around an outer surface of a treatment device upon deployment while a circular cross-section of the tubular body radially expands. Embolic filtering system 900 thus includes a delivery catheter 901 having a sheath 902 to cover and restrain filter 930 into a radially compressed and generally straightened delivery configuration (not shown) to provide a low or minimized delivery profile. Elongate shaft 918 having filter 930 mounted at the distal end thereof slidably extends through sheath 902. When sheath 902 is retracted, filter 930 assumes the fully deployed/expanded configuration shown in FIG. 9.

Similar to filter 130 described above, in its fully deployed configuration, filter 930 has a predetermined or heat-set shape in which tubular body 931 of filter 930 coils into a series of one or more loops 924, thereby spiraling or winding around an outer surface of an independent treatment device (not shown in FIG. 9) in a corkscrew fashion. However, rather than having consecutive loops with the same expanded, outer diameter as described above with filter 130, the outer diameters of consecutive loops 924 of filter 930 gradually increase relative to illustrative blood flow direction indicated by arrow 950. In an alternate embodiment, the outer diameters of consecutive loops 924 of filter 930 may gradually decrease relative to the blood flow direction indicated by arrow 950. The coiled tubular body 931 of deployed filter 930 thus forms a longitudinally-extending conical or flared profile. Other filter configurations in which an outermost diameter of the deployed filter shape conforms to the vessel wall and an innermost diameter of the deployed filter shape conforms to an outer surface of an independent treatment device may be utilized without departing from the spirit and scope of the invention. In addition, the deployed filter shape may be modified such as to not include a longitudinal opening defined by an innermost diameter such that the filter may be utilized as a distal protection device that is deployable in a location or manner that does not result in contact with the treatment device.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A device for collecting embolic debris in a vessel in a patient, comprising:
   a self-expanding filter having a tubular body that includes openings therein for receiving the embolic debris there through and for allowing perfusion, the tubular body having a generally circular cross-section and an interior surface that defines an interior volume for collecting the embolic debris,
   wherein when the filter is in a delivery configuration the tubular body is substantially cylindrical and
   wherein when the filter is in a deployed configuration the tubular body coils to form a series of one or more loops for collecting the embolic debris within respective interior volumes thereof,
   whereby the generally circular cross-section of the tubular body is maintained in each loop such that a portion of the interior volume of the tubular body defines the respective interior volume of each loop thereof, and such that an outermost surface of the one or more loops defines an abluminal surface of the coiled tubular body having an expanded outer diameter for conforming to an inner wall of the vessel and an innermost surface of the one or more loops defines an adluminal surface of the coiled tubular body defining a longitudinal opening through the filter.

2. The device of claim 1, wherein the filter is constructed from a material selected from the group consisting of stainless steel, nitinol, and a super alloy.

3. The device of claim 1, wherein the filter includes first openings and second openings, wherein the second openings are of a smaller dimension than the first openings.

4. The device of claim 3, wherein the first openings are sized to allow entry of dislodged embolic debris into the device.

5. The device of claim 4, wherein the second openings are sized to retain the dislodged embolic debris within the device.

6. The device of claim 1, wherein the inner surface of the coiled tubular body conforms to an outer surface of an independent treatment device that extends through the longitudinal opening.

7. The device of claim 1, wherein consecutive loops of the coiled tubular body have equal expanded outer diameters.

8. The device of claim 1, wherein consecutive loops of the coiled tubular body have unequal expanded outer diameters.

9. The device of claim 1, wherein the tubular body is formed from a plurality of braided filaments and the openings are the interstices between the braided filaments.

10. The device of claim 9, wherein the tubular body is covered by a tubular membrane or film having openings therein.

11. An embolic filtering system for collecting embolic debris in a vessel of a patient, comprising:
a delivery catheter including an outer sheath and an inner sheath extending slidably through a lumen of the outer sheath;
a filter including an elongate shaft and a self-expanding tubular body that includes openings therein for receiving the embolic debris there through and for allowing perfusion, the tubular body having a generally circular cross-section and an interior surface that defines an interior volume for collecting the embolic debris, the tubular body being mounted at a distal end of the elongate shaft, the filter extending slidably through a lumen of the inner sheath and having
a delivery configuration wherein the tubular body is substantially cylindrical, and
a fully deployed configuration wherein the tubular body coils to form a series of one or more loops with a respective interior volume defined within each loop being disposed for collecting the embolic debris therein, whereby the generally circular cross-section of the tubular body is maintained in each loop such that a portion of the interior volume of the tubular body defines the respective interior volume of each loop thereof, and wherein an abluminal surface of the coiled tubular body has an expanded outer diameter for conforming to an inner wall of the vessel and an adluminal surface of the coiled tubular body defines a longitudinal opening through the filter sized to conform to an outer surface of an independent treatment device.

12. The embolic filtering system of claim 11, wherein the outer sheath holds the filter in the substantially cylindrical delivery configuration.

13. The embolic filtering system of claim 12, wherein the inner sheath radially constrains an outer diameter of the tubular body of the filter when the outer sheath is withdrawn.

14. The embolic filtering system of claim 13, wherein the inner sheath has a preformed coil shape that is substantially cylindrical when constrained by the outer sheath and returns to a substantially helical or coil shape when the outer sheath is retracted.

15. The embolic filtering system of claim 11, wherein in a partially deployed configuration the tubular body of the filter radially constrained by the inner sheath is disposed in the series of one or more coiled loops around the outer surface of the independent treatment device.

16. The embolic filtering system of claim 11, wherein the filter is constructed from a material selected from the group consisting of stainless steel, nitinol, and super alloy and includes first openings sized to allow entry of dislodged embolic debris into at least one coiled loop of the filter and second openings sized to retain the dislodged embolic debris within the at least one coiled loop.

17. The embolic filtering system of claim 11, wherein the tubular body is formed from a plurality of braided filaments and the openings are the interstices between the braided filaments.

18. The embolic filtering system of claim 17, wherein the tubular body is covered by a tubular membrane or film having openings therein.

* * * * *